US012746061B2

(12) United States Patent
Akerele-Ale et al.

(10) Patent No.: US 12,746,061 B2
(45) Date of Patent: Sep. 29, 2026

(54) CATHETERS, SYSTEMS, AND METHODS FOR ENDOVASCULAR TREATMENT OF A BLOOD VESSEL

(71) Applicant: TVA MEDICAL, INC., Franklin Lakes, NJ (US)

(72) Inventors: Oladipo Peter Akerele-Ale, Franklin Lakes, NJ (US); Alex Palmer, Franklin Lakes, NJ (US); Olivia Palmer, Franklin Lakes, NJ (US); Stephen Pede, Franklin Lakes, NJ (US); Breanna Simpson, Franklin Lakes, NJ (US)

(73) Assignee: TVA MEDICAL, INC., Franklin Lakes, NJ (US)

( * ) Notice: Subject to any disclaimer, the term of this patent is extended or adjusted under 35 U.S.C. 154(b) by 220 days.

(21) Appl. No.: 18/695,680

(22) PCT Filed: Sep. 30, 2021

(86) PCT No.: PCT/US2021/052936
§ 371 (c)(1),
(2) Date: Mar. 26, 2024

(87) PCT Pub. No.: WO2023/055381
PCT Pub. Date: Apr. 6, 2023

(65) Prior Publication Data

US 2024/0390063 A1 Nov. 28, 2024

(51) Int. Cl.

| | |
|---|---|
| ***A61B 18/14*** | (2006.01) |
| ***A61B 18/00*** | (2006.01) |
| ***A61B 90/00*** | (2016.01) |

(52) U.S. Cl.
CPC .......... *A61B 18/1492* (2013.01); *A61B 90/08* (2016.02); *A61B 2018/00297* (2013.01);
(Continued)

(58) Field of Classification Search
CPC ...... A61B 18/1492; A61B 2017/00477; A61B 2017/00876; A61B 2018/00297; A61B 2018/00404; A61B 2018/00577; A61B 2018/00625; A61B 2018/1405; A61B 2018/144; A61B 2018/1465; A61B 2018/1475; A61B 2090/0811;
(Continued)

(56) References Cited

U.S. PATENT DOCUMENTS

2014/0276335 A1* 9/2014 Pate .................... A61M 1/3655 604/8
2015/0080886 A1* 3/2015 Miller ................ A61B 18/1492 606/41
2021/0022758 A1* 1/2021 Herlinger .......... A61M 25/0133

FOREIGN PATENT DOCUMENTS

WO 2017124062 A1 7/2017

* cited by examiner

*Primary Examiner* — Tigist S Demie
(74) *Attorney, Agent, or Firm* — Dickinson Wright PLLC; Andrew D. Dorisio; Nicholas P. Coleman

(57) ABSTRACT

A catheter for endovascular treatment of a blood vessel includes a treatment portion, a proximal magnetic array positioned proximal to the treatment portion, and a distal magnetic array positioned distal to the treatment portion. Each of the proximal magnetic array and the distal magnetic array include a first magnetic segment having a first polarity, and a second magnetic segment having a second polarity opposite to the first polarity, wherein the second magnetic segment is disposed adjacent to the treatment portion.

21 Claims, 6 Drawing Sheets

(52) U.S. Cl.
CPC ............... *A61B 2018/00404* (2013.01); *A61B 2018/00577* (2013.01); *A61B 2018/1405* (2013.01); *A61B 2090/0811* (2016.02)

(58) Field of Classification Search
CPC . A61B 2090/3937; A61B 90/08; A61B 90/39; A61M 25/0127; A61M 25/04
See application file for complete search history.

CATHETERS, SYSTEMS, AND METHODS FOR ENDOVASCULAR TREATMENT OF A BLOOD VESSEL

TECHNICAL FIELD

The present disclosure relates to catheters, systems, and methods for endovascular treatments of a blood vessel, and more particularly catheters, systems, and methods for having alignment elements for aligning catheters for forming a fistula or providing other endovascular treatment.

BACKGROUND

Endovascular treatments of a blood vessel may include fistula formation. A fistula is generally a passageway formed between two internal organs (e.g., blood vessels or other bodily organs). Forming a fistula between two blood vessels can have one or more beneficial functions. For example, the formation of a fistula between an artery and a vein may provide access to the vasculature for hemodialysis patients. Specifically, forming a fistula between an artery and a vein allows blood to flow quickly between the vessels while bypassing the capillaries. In other instances, a fistula may be formed between two veins to form a veno-venous fistula. Generally, arterio-venous fistula formation requires surgical dissection of a target vein, and transecting and moving the vein for surgical anastomosis to the artery. It may therefore be useful to find less invasive and reliable devices and methods for aligning blood vessels and forming a fistula between the aligned blood vessels.

SUMMARY

One challenging aspect of forming a fistula (endovascular treatment) between blood vessels, though other body vessels are contemplated and possible, is properly aligning and coapting catheters in adjacent blood vessels prior to fistula formation. Embodiments of the present disclosure are directed to systems, methods, and catheters for fistula formation that provide improved catheter alignment and coaptation as will be described in greater detail below.

In one embodiment, a catheter for endovascular treatment of a blood vessel includes a treatment portion, a proximal magnetic array positioned proximal to the treatment portion, and a distal magnetic array positioned distal to the treatment portion. Each of the proximal magnetic array and the distal magnetic array include a first magnetic segment having a first polarity, and a second magnetic segment having a second polarity opposite to the first polarity, wherein the second magnetic segment is disposed adjacent to the treatment portion.

In another embodiment, a system for endovascular treatment of a blood vessel includes a first catheter and a second catheter. Each of the first catheter and the second catheter include a treatment portion, a proximal magnetic array positioned proximal to the treatment portion, and a distal magnetic array positioned distal to the treatment portion. Each proximal magnetic array and each distal magnetic array includes a first magnetic segment having a first polarity, and a second magnetic segment having a second polarity opposite to the first polarity. The second magnetic segments are disposed adjacent to the treatment portion. The second polarity of second magnetic segment of the first catheter has a same polarity orientation as the second magnetic segment of the second catheter when the first catheter and the second catheter are aligned for endovascular treatment.

In yet another embodiment, a method for endovascular treatment of a blood vessel includes advancing a first catheter within a first blood vessel to a treatment location, aligning a treatment portion of the first catheter with the treatment location, and modifying the first blood vessel at the treatment location with the treatment portion. The first catheter includes a proximal magnetic array positioned proximal to the treatment portion, and a distal magnetic array positioned distal to the treatment portion. Each of the proximal magnetic array and the distal magnetic array includes a first magnetic segment having a first polarity, and a second magnetic segment having a second polarity opposite to the first polarity, the second magnetic segment being disposed adjacent to the treatment portion.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

Reference will now be made in greater detail to various embodiments of the present disclosure, some embodiments of which are illustrated in the accompanying drawings. Whenever possible, the same reference numerals will be used throughout the drawings to refer to the same or similar parts.

DETAILED DESCRIPTION

Embodiments described herein are directed to devices, systems, and methods for endovascular treatment of a blood vessel such as, but not limited to forming a fistula, wire crossing procedures, bypass procedures, etc. For example, a catheter may be placed in each of two adjacent blood vessels to form a fistula therebetween with the catheters. However, flexibility of the catheters, spacing of vessels, thickness of the vessel walls, and/or the tortuous anatomy of the vessels, may make it difficult to provide sufficient coaptation and/or alignment between vessels for fistula formation. Embodiments of the present disclosure provide improved alignment and coaptation thereby providing improved, reliable treatment. For example, in some embodiments, a catheter for endovascular treatment of a blood vessel according to the present disclosure includes a treatment portion, a proximal magnetic array positioned proximal to the treatment portion, and a distal magnetic array positioned distal to the treatment portion. Each of the proximal magnetic array and the distal magnetic array may include a first magnetic segment having a first polarity and a second magnetic segment having a second polarity opposite to the first polarity, wherein the second magnetic segments are disposed adjacent to the treatment portion. The opposite poled magnetic segment may allow for generation of tactile feedback to guide a user in proper alignment and/or coaptation of the first catheter with a second catheter placed in an adjacent vessel, thereby allowing a physician to easily confirm alignment and/or coaptation of the catheters. These and additional features and benefits will be described in greater detail herein.

Figure 1:
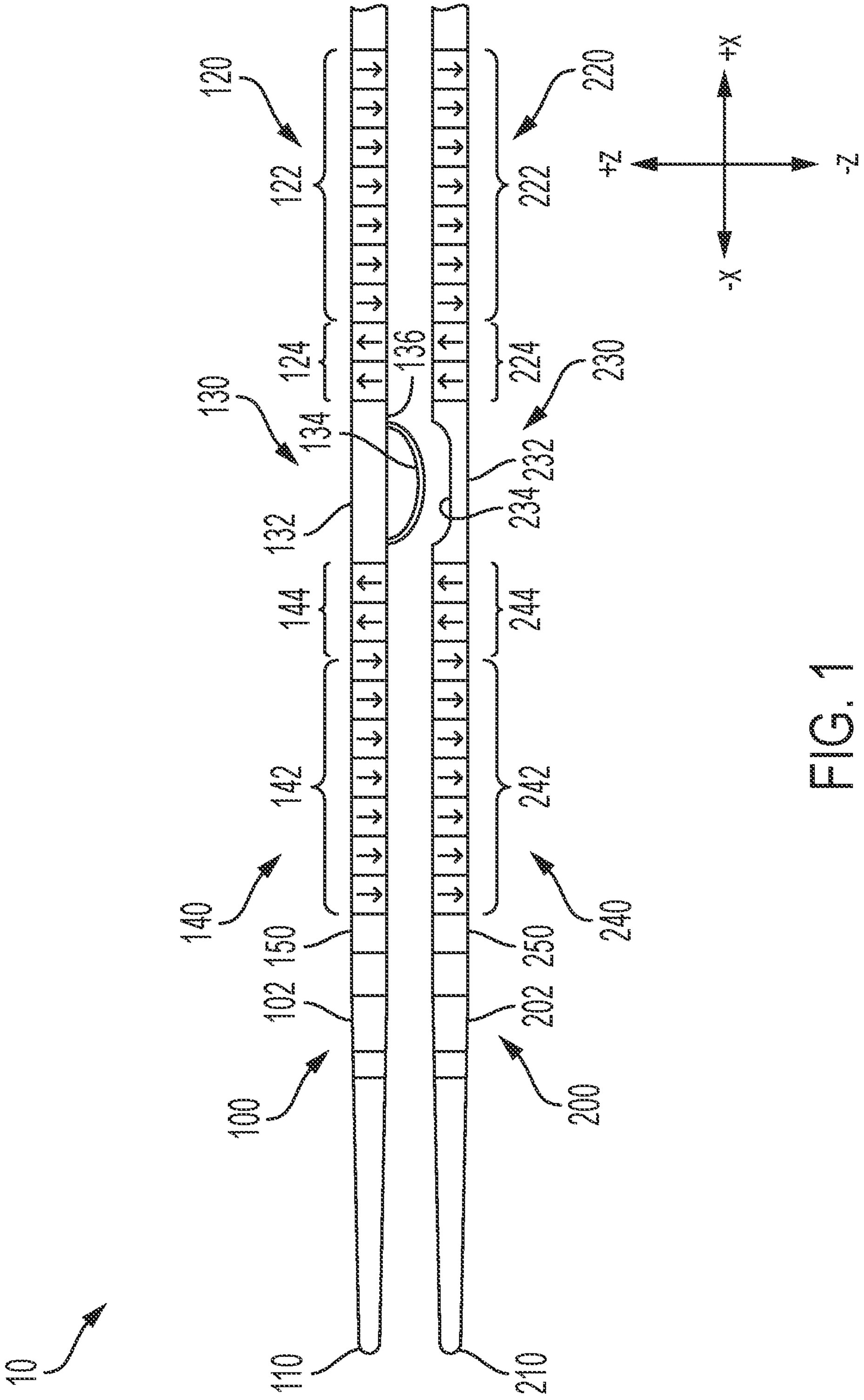
FIG. 1 schematically depicts a system of catheters for endovascular treatment of a blood vessel, according to one or more embodiments shown and described herein.

Referring now to FIG. 1, a system 10 for providing endovascular treatment of a blood vessel, such as a fistula formation, is schematically depicted. The system 10 may include a first catheter 100 and a second catheter 200. It may be appreciated that the first catheter 100 and the second catheter 200 are substantially similar to one another. Accordingly, description of the first catheter 100 generally applies to the second catheter 200 unless otherwise noted or apparent. It is noted that the first catheter 100 and the second catheter 200 may be provided within a kit and/or separately from one another.

The first catheter 100 generally includes a catheter body 102, a treatment portion 130, a proximal magnetic array 120, and a distal magnetic array 140. It is noted that the first catheter 100 may include a greater or fewer number of components without departing from the scope of the present disclosure.

The catheter body 102 may be sized to be advanced through a blood vessel and may include a distal tip 110 that is may be shaped and/or sized to aid in advancement of the first catheter 100 through a blood vessel. For example, the distal tip 110 may be pointed, tapered, and/or atraumatic for advancement through a blood vessel. The catheter body 102 may have any cross-sectional shape and any diameter suitable for intravascular use. The first catheter 100 may include or define one or more lumens or other passageways (not shown) extending at least partially along or through the catheter body 102. For instance, the one or more lumens may extend at least partially longitudinally through the catheter body 102 in the direction of an x-axis of the depicted coordinate axes of FIG. 1. The catheter body 102 may be formed of any material or combination of materials able to be traversed through a vasculature of a body. For example, the catheter body 102 may include, silicone, rubber, etc.

As noted above, the first catheter 100 may have a treatment portion 130 for endovascular treatment of a blood vessel. In embodiments, the treatment portion 130 may have a housing 132 and a fistula-forming element 134. In embodiments, the fistula-forming element 134 may be an electrode, such as a leaf spring electrode, having an exposed ablation surface. The fistula-forming element 134 may be coupled to a power source (not shown), such as via a lead wire or other conductor attached thereto. When activated, current may be supplied to and/or carried from tissue and fluid via the ablation surface to facilitate ablation or vaporization of tissue to form a fistula.

In some embodiments, the fistula-forming element 134 may be a spring wire or leaf spring electrode, which may be movable between a retracted configuration, in which the fistula-forming element 134 is retained within the first catheter 100, and a protruding configuration, in which the fistula-forming element 134 projects beyond the outer surface 136 of the catheter body 102. The fistula-forming element 134 may or may not be naturally biased to project from the housing 132. When the fistula-forming element 134 is naturally biased to project from the housing 132, a structure, such as a sleeve (not shown), may be used to hold or maintain the fistula-forming element 134 in a retracted configuration until deployment is desired. In some embodiments, the fistula-forming element 134 may be manually advanced or retracted such as via a lead wire which may be coupled to the fistula-forming element 134 which may be manually pulled or pushed to retract or advance the fistula-forming element 134. In some embodiments, the first catheter 100 may comprise one or more insulating materials (not shown) which may shield or otherwise protect the first catheter 100 and its components from heat generated by the fistula-forming element 134 during use. For example, one or more portions of the housing 132 may have one or more heat insulating portions which may include ceramic.

As depicted, the fistula-forming element 134 may be arc shaped, though other shapes are contemplated and possible (e.g., rectangular, square, angular, etc.). The size and shape of the fistula-forming element 134 may be varied based on factors including tissue thickness and density, as well as desired fistula size, shape, and location. It is noted that the fistula-forming element 134 is not limited to an electrode as describe above, but may include a different cutting/ablation device such as, but not limited to, any electrocautery mechanism, blades, lances, needles, cryogenic-cautery devices, ultrasonic-cautery devices, laser ablation devices, etc.

Still referring to FIG. 1 and as noted above, the first catheter 100 may have a proximal magnetic array 120 arranged on or within the catheter body 102 proximal to and adjacent the treatment portion 130. The proximal magnetic array 120 may include a plurality of magnetic elements arranged in a longitudinal array along a length of the catheter. The proximal magnetic array 120 may include a first magnetic segment 122 including a first portion of the plurality of magnetic elements and a second magnetic segment 124 including a second portion of the plurality of magnetic elements. Each magnetic segment may have a polarity such as shown (e.g., indicated via up/down arrows indicating a direction of polarity) such that the first magnetic segment 122 includes a first polarity and the second magnetic segment 124 includes a second polarity. In embodiments, the first magnetic segment 122 may have an opposite polarity to the second magnetic segment 124. It will be appreciated that the polarity direction shown in the figures is for illustrative purposes and the polarity directions of the first and second magnetic segments 122 and 124 may be any suitable direction. For example, the magnetic elements of the first magnetic segment 122 may have a north magnetic pole facing along the −Z direction of the depicted coordinate axes of FIG. 1 and the second magnetic segment 124 may have a north magnetic pole facing the +Z direction, or vice versa.

Each of the magnetic elements of the plurality of magnetic elements of the first magnetic segment 122 and the second magnetic segment 124 may having substantially the same dimensions (e.g., height, width, and depth) and substantially the same magnetic strength. In some embodiments, magnetic elements may have a combination of different sized magnets, different shaped magnets, and/or magnets of differing magnetic strength. For example, the individual magnetic elements may have a substantially cubic shape, circular shape, oval shape, or any shape configured to fit within a targeted blood vessel.

In some embodiments, the number of the plurality of magnetic elements of the first magnetic segment 122 and/or the second magnetic segment 124 may be modified for optimization of magnetic strength for alignment or coaptation purposes. The first magnetic segment 122 and/or the second magnetic segment 124 may comprise any number of individual magnetic elements including one or more magnetic elements. Moreover, each catheter may comprise any number of individual magnetic elements (e.g., one, two, three, four, five, six, seven, or eight or more, etc.). In embodiments, the first magnetic segment 122 and the second magnetic segment 124 have different lengths (e.g., different numbers of magnetic elements). For example, the first magnetic segment 122 may have a length that is longer than a length of the second magmatic segment 124. For example, the second magnetic segment 124 may have one to four magnetic elements, such as at least two magnetic elements, and the first magnetic segment 122 may have twenty-six to thirty magnetic elements. For example, the first magnetic segment 122 may have twenty-eight magnetic elements, and the second magnetic segment 124 may have two magnetic elements. That is, the first magnetic segment 122 may have a greater number of magnetic elements than the second magnetic segment 124, such that the first magnetic segment 122 is axially longer than the second magnetic segment 124. In another embodiment, the second magnetic segment 124 may have more magnetic elements than the first magnetic segment 122. In other words, the second magnetic segment 124 may be axially longer than the first magnetic segment 122 along X direction of the depicted coordinate axes.

In the depicted embodiment, the first magnetic segment 122 is continuous so as not to be interrupted by intervening magnetic elements having a different polarity. Similarly the second magnetic segment 124 may be positioned directly adjacent the second magnetic element and may be continuous so as not to be interrupted by intervening magnetic elements having a different polarity. In the depicted embodiment, the second magnetic segment 124 is positioned distal to the first magnetic segment 122 and is positioned between the first magnetic segment 122 and the treatment portion 130.

Still referring to FIG. 1 and as noted above, the first catheter 100 includes a distal magnetic array 140 arranged on or within the catheter body 102 distal to and adjacent the treatment portion 130. The distal magnetic array 140 may include a plurality of magnetic elements (e.g., individual magnets) arranged in a longitudinal array along a length of the catheter. The distal magnetic array 140 may include a first magnetic segment 142 including a first portion of the plurality of magnetic elements and a second magnetic segment 144 including a second portion of the plurality of magnetic elements. Each magnetic segment may have a polarity such as shown (e.g., indicated via up/down arrows indicating a direction of polarity) such that the first magnetic segment 142 includes a first polarity and the second magnetic segment 144 includes a second polarity. In embodiments, the first magnetic segment 142 may have the opposite polarity to the second magnetic segment 144. It will be appreciated that the polarity direction shown in the figures is for illustrative purposes and the polarity directions of the first and second magnetic segments 142 and 144 may be any suitable direction. For example, the first magnetic segment 142 may have a north magnetic pole facing along the −Z direction of the depicted coordinate axes of FIG. 1 and the second magnetic segment 144 may have a north magnetic pole facing the +Z direction, or vice versa.

Each of the magnetic elements of the plurality of magnetic elements of the first magnetic segment 142 and the second magnetic segment 144 may having substantially the same dimensions (e.g., height, width, and depth) and substantially the same magnetic strength. In some embodiments, magnetic elements may have a combination of different sized magnets, different shaped magnets, and/or magnets of differing magnetic strength. For example, the individual magnetic elements may have a substantially cubic shape, circular shape, oval shape, or any shape configured to fit within a targeted blood vessel.

In some embodiments, the number of the plurality of magnetic elements of the first magnetic segment 142 and/or the second magnetic segment 144 may be modified for optimization of magnetic strength for alignment or coaptation purposes. The first magnetic segment 142 and/or the second magnetic segment 144 may comprise any number of individual magnetic elements including one or more magnetic elements. Moreover, each catheter may comprise any number of individual magnetic elements (e.g., one, two, three, four, five, six, seven, or eight or more, etc.). In embodiments, the first magnetic segment 142 and the second magnetic segment 144 have different lengths (e.g., different numbers of magnetic elements). For example, the first magnetic segment 142 may have a length that is longer than a length of the second magmatic segment 144. For example, the second magnetic segment 144 may have one to four magnetic elements, such as at least two magnetic elements, and the first magnetic segment 142 may have twenty-six to thirty magnetic elements. For example, the first magnetic segment 142 may have twenty-eight magnetic elements, and the second magnetic segment 144 may have two magnetic elements. That is, the first magnetic segment 142 may have a greater number of magnetic elements than the second magnetic segment 144, such that the first magnetic segment 142 is axially longer than the second magnetic segment 144. In another embodiment, the second magnetic segment 144 may have more magnetic elements than the first magnetic segment 142. In other words, the second magnetic segment 144 may be axially longer than the first magnetic segment 142 along X direction of the depicted coordinate axes.

In the depicted embodiment, the first magnetic segment 142 is continuous so as not to be interrupted by intervening magnetic elements having a different polarity. Similarly the second magnetic segment 144 may be positioned directly adjacent the first magnetic segment 142 and may be continuous so as not to be interrupted by intervening magnetic elements having a different polarity. In the depicted embodiment, the second magnetic segment 144 is positioned distal to and immediately proximate the treatment portion 130 such that the second magnetic segment 144 is positioned between the treatment portion 130 and the first magnetic segment 142.

Accordingly, each of the second magnetic segments 124 and 144 of the proximal magnetic array 120 and the distal magnetic array 140 may be disposed directly adjacent to the treatment portion 130. It is noted that in some embodiments, the second magnetic segments 124 and 144 may not be positioned directly adjacent the treatment portion 130 but may be spaced from the treatment portion 130 such as either by the first magnetic segments 122, 142 or a third magnetic segment (not shown). In embodiments, the magnetic poles of the first magnetic segment 122 may be arranged in the same manner with respect to the magnetic pole of the first segment 142, and the magnetic pole of second magnetic segment 124 may be arranged in the same manner with respect to the magnetic pole of the second magnetic segment 144. That is the first magnetic segments 122, 142 may have the same polarity orientation (e.g., North pointing in the −Z direction of the depicted coordinate axes) and the second magnetic segments 124, 144 may have the same polarity orientation though facing opposite the polarity orientation of the first magnetic segments 122, 142 (e.g., North pointing the +Z direction of the depicted coordinate axes).

Similar to the first catheter 100, the second catheter 200 generally includes a catheter body 202, a treatment portion 230, a proximal magnetic array 220, and a distal magnetic array 240. It is noted that the second catheter 200 may include a greater or fewer number of components without departing from the scope of the present disclosure.

The catheter body 202 may include a distal tip 210 that is may be shaped and/or sized to aid in advancement of the second catheter 200 through a blood vessel. For example, the distal tip 210 may be pointed, tapered, and/or atraumatic for advancement through a blood vessel. The catheter body 202 may have any cross-sectional shape and any diameter suitable for intravascular use. The second catheter 200 may include or define one or more lumens or other passageways (not shown) extending at least partially along or through the catheter body 202. For instance, the one or more lumens may extend at least partially longitudinally through the catheter body 202 in the direction of an X-axis of the depicted coordinate axes of FIG. 1. The catheter body 202 may be formed of any material or combination of materials able to be traversed through a vasculature of a body. For example, the catheter body 202 may include, silicone, rubber, etc.

As noted above, the second catheter 200 may have a treatment portion 230 that may be configured to be aligned or coapted with the treatment portion 130 of the first catheter 100 such as when the first catheter 100 and the second catheter 200 are aligned in adjacent vessels. The treatment portion 230 may define a backstop 232, which may be configured to receive the fistula-forming element 134 as it passes through tissue of the adjacent vessels to form a fistula. The backstop 232 may have a shape (e.g., a concave portion 234) that corresponds to and is complementary (e.g., inverse, reciprocal) to the fistula-forming element 134 to match and conform to the fistula-forming element 134 when the treatment portions 130 and 230 are aligned and/or coapted. The concave portion 234 may be electrically conductive and/or electrically insulative. For example, where electrically conductive, the concave portion 234 may act as an extension of the fistula-forming element 124 (e.g., where the fistula-forming element includes an electrode) to aid in ablation or removal of tissue. Where electrically insulative, the concave portion 234 may insulate portions of the body and/or second catheter 200 from electrical contact where the fistula-forming element 134 is an electrode. The size and shape of the backstop 232 may be varied based on factors including tissue thickness and density, as well as desired fistula size, shape, and location.

The treatment portion 230 may have any suitable length along the second catheter 200. In embodiments, the treatment portion 230 may have substantially the same length as the treatment portion 130. While shown in FIG. 1 as having a concave portion 234, it should also be appreciated that in some variations, the treatment portion 230 of the second catheter 200 may not include a concave portion 234. In some variations, the treatment portion 230 of the second catheter 200 may include the fistula-forming element (not shown), such as described hereinabove, in addition to or instead of the first catheter 100 having the fistula-forming element 134. Accordingly in some embodiments, the first and second catheters 100, 200 may be substantially identical to one another.

Still referring to FIG. 1 and as noted above, the second catheter 200 may have a proximal magnetic array 220 arranged on or within the catheter body 202 proximal to and adjacent the treatment portion 230. The proximal magnetic array 220 which may include a plurality of magnetic elements arranged in a longitudinal array along a length of the catheter. The proximal magnetic array 220 may include a first magnetic segment 222 including a first portion of the plurality of magnetic elements and a second magnetic segment 224 including a second portion of the plurality of magnetic elements. Each magnetic segment may have a polarity such as shown (e.g., indicated via up/down arrows indicating a direction of polarity) such that the first magnetic segment 222 includes a first polarity and the second magnetic segment 224 includes a second polarity. In embodiments, the first magnetic segment 222 may have the opposite polarity to the second magnetic segment 224. It will be appreciated that the polarity direction shown in the figures is for illustrative purposes and the polarity directions of the first and second magnetic segments 222 and 224 may be any suitable direction. For example, the first magnetic segment 222 may have a north magnetic pole facing along the −Z direction of the depicted coordinate axes of FIG. 1 and the second magnetic segment 124 may have a north magnetic pole facing the +Z direction, or vice versa.

Each of the magnetic elements of the plurality of magnetic elements of the first magnetic segment 222 and the second magnetic segment 224 may have substantially the same dimensions (e.g., height, width, and depth) and substantially the same magnetic strength. In some embodiments, magnetic elements may have a combination of different sized magnets, different shaped magnets, and/or magnets of differing magnetic strength. For example, the individual magnetic elements may have a substantially cubic shape, circular shape, oval shape, or any shape configured to fit within a targeted blood vessel.

The number of the plurality of magnetic elements of the first magnetic segment 222 and/or the second magnetic segment 224 may be modified for optimization of magnetic strength for alignment or coaptation purposes. The first magnetic segment 222 and/or the second magnetic segment 224 may comprise any number of individual magnetic elements including one or more magnetic elements. Moreover, the catheter may comprise any number of individual magnetic elements (e.g., one, two, three, four, five, six, seven, or eight or more, etc.). In embodiments, the first magnetic segment 222 and the second magnetic segment 224 have different lengths (e.g., different numbers of magnetic elements). For example, the first magnetic segment 222 may have a length that is longer than a length of the second magmatic segment 224. For example, the second magnetic segment 224 may have one to four magnetic elements, such as at least two magnetic elements, and the first magnetic segment 222 may have twenty-six to thirty magnetic elements. For example, the first magnetic segment 222 may have twenty-eight magnets, and the second magnetic segment 224 may have two magnets. That is, the first magnetic segment 222 may have a greater number of magnetic elements than the second magnetic segment 224, such that the first magnetic segment 222 is axially longer than the second magnetic segment 224. In another embodiment, the second magnetic segment 224 may have more magnets than the first magnetic segment 222. In other words, the second magnetic segment 124 may be axially longer than the first magnetic segment 222 along X direction of the depicted coordinate axes.

In the depicted embodiment, the first magnetic segment 222 is continuous so as not to be interrupted by intervening magnetic elements having a different polarity. Similarly the second magnetic segment 224 may be positioned directly adjacent the second magnetic element and may be continuous so as not to be interrupted by intervening magnetic elements having a different polarity. In the depicted embodiment, the second magnetic segment 224 is positioned distal to the first magnetic segment 222 and is positioned between the first magnetic segment 222 and the treatment portion 230.

The second catheter 200 includes a distal magnetic array 140 arranged on or within the catheter body 202 distal to and adjacent the treatment portion 230. The distal magnetic array 240 may include a first magnetic segment 242 including a first portion of the plurality of magnetic elements and a second magnetic segment 244 including a second portion of the plurality of magnetic elements. Each magnetic segment may have a polarity such as shown (e.g., indicated via up/down arrows indicating a direction of polarity) such that the first magnetic segment 242 includes a first polarity and the second magnetic segment 244 includes a second polarity. In embodiments, the first magnetic segment 242 may have the opposite polarity to the second magnetic segment 244. It will be appreciated that the polarity direction shown in the figures is for illustrative purposes and the polarity directions of the first and second magnetic segments 242 and 244 may be any suitable direction. For example, the first magnetic segment 242 may have a north magnetic pole facing along the −Z direction of the depicted coordinate axes of FIG. 1 and the second magnetic segment 244 may have a north magnetic pole facing the +Z direction, or vice versa.

Each of the magnetic elements of the plurality of magnetic elements of the first magnetic segment 242 and the second magnetic segment 244 may having substantially the same dimensions (e.g., height, width, and depth) and substantially the same magnetic strength. In some embodiments, magnetic elements may have a combination of different sized magnets, different shaped magnets, and/or magnets of differing magnetic strength. For example, the individual magnetic elements may have a substantially cubic shape, circular shape, oval shape, or any shape configured to fit within a targeted blood vessel.

In some embodiments, the number of the plurality of magnetic elements of the first magnetic segment 242 and/or the second magnetic segment 244 may be modified for optimization of magnetic strength for alignment or coaptation purposes. The first magnetic segment 242 and/or the second magnetic segment 244 may comprise any number of individual magnetic elements including one or more magnetic elements. Moreover, and as noted above, each catheter may comprise any number of individual magnetic elements (e.g., one, two, three, four, five, six, seven, or eight or more, etc.). In embodiments, the first magnetic segment 242 and the second magnetic segment 244 have different lengths (e.g., different numbers of magnetic elements). For example, the first magnetic segment 242 may have a length that is longer than a length of the second magmatic segment 244. For example, the second magnetic segment 224 may have one to four magnetic elements, such as at least two magnetic elements, and the first magnetic segment 242 may have twenty-six to thirty magnetic elements. For example, the first magnetic segment 242 may have twenty-eight magnets, and the second magnetic segment 244 may have two magnets. That is, the first magnetic segment 242 may have a greater number of magnetic elements than the second magnetic segment 244, such that the first magnetic segment 242 is axially longer than the second magnetic segment 244. In another embodiment, the second magnetic segment 244 may have more magnets than the first magnetic segment 242. In other words, the second magnetic segment 244 may be axially longer than the first magnetic segment 242 along X direction of the depicted coordinate axes.

In the depicted embodiment, the first magnetic segment 242 is continuous so as not to be interrupted by intervening magnetic elements having a different polarity. Similarly the second magnetic segment 244 may be positioned directly adjacent the first magnetic segment 242 and may be continuous so as not to be interrupted by intervening magnetic elements having a different polarity. In the depicted embodiment, the second magnetic segment 224 is positioned distal to and immediately proximate the treatment portion 230 such that the second magnetic segment 224 is positioned between the treatment portion 230 and the first magnetic segment 222.

Accordingly, the second magnetic segments 224 and 244 of the proximal magnetic array 220 and the distal magnetic array 240 may be disposed directly adjacent to the treatment portion 230. It is noted that in some embodiments, the second magnetic segments 224 and 244 may not be positioned directly adjacent the treatment portion 230 but may be spaced from the treatment portion 230 such as either by the first magnetic segments 222, 224 or a third magnetic segment (not shown). In embodiments, the magnetic poles of the first magnetic segment 222 may be arranged in the same manner with respect to the magnetic pole of the first magnetic segment 242, and the magnetic pole of second magnetic segment 224 may be arranged in the same manner with respect to the magnetic pole of the second magnetic segment 244. That is the first magnetic segments 222, 242 may have the same polarity orientation (e.g., North pointing in the −Z direction of the depicted coordinate axes) and the second magnetic segments 224, 244 may have the same polarity orientation though facing opposite the polarity orientation of the first magnetic segments 222, 242 (e.g., North pointing the +Z direction of the depicted coordinate axes).

The polarity of magnets described herein is not limited to the above mentioned exemplary embodiments as long as proximal magnetic array 120 of a first catheter 100 and proximal magnetic array 220 of a second catheter 200 attract each other, and distal magnetic array 140 of the first catheter 100 and distal magnetic array 240 of the second catheter 200 attract each other when the treatment portions 130, 230 are aligned for vascular treatment, such as fistula formation.

In view of the above, the magnetic pole of the first magnetic segments 122, 222 and 142, 242 of the first and second catheters 100, 200 may be arranged to attract one another, and the magnetic pole of second magnetic segments 124, 224 and 144, 244 may be arranged to attract one another. However, the first magnetic segments 122, 142, 222, 242 are arranged to repel the second magnetic segments 124, 144, 224, 244 of the opposite catheter. Accordingly, as the catheters 100, 200 are advanced relative to one another the catheters 100, 200 will at least partially repel one another until proper alignment of the treatment portions 130, 230 is achieved. Upon reaching proper alignment, the attraction between the first catheter 100 and the second catheter 200 will provide tactile feedback (due to the change in attraction between the first catheter 100 and the second catheter 200 when alignment is reached) to indicate to a user that proper alignment between the treatment portions 130, 230 is achieved. The location of the second portions 124, 144, 224, 244 being directly adjacent the treatment portions 130, 230 may aid in concentrating a location of improved magnetic attraction closest to the treatment portions 130, 230, which may aid in providing increased tactile feedback.

Figure 2:
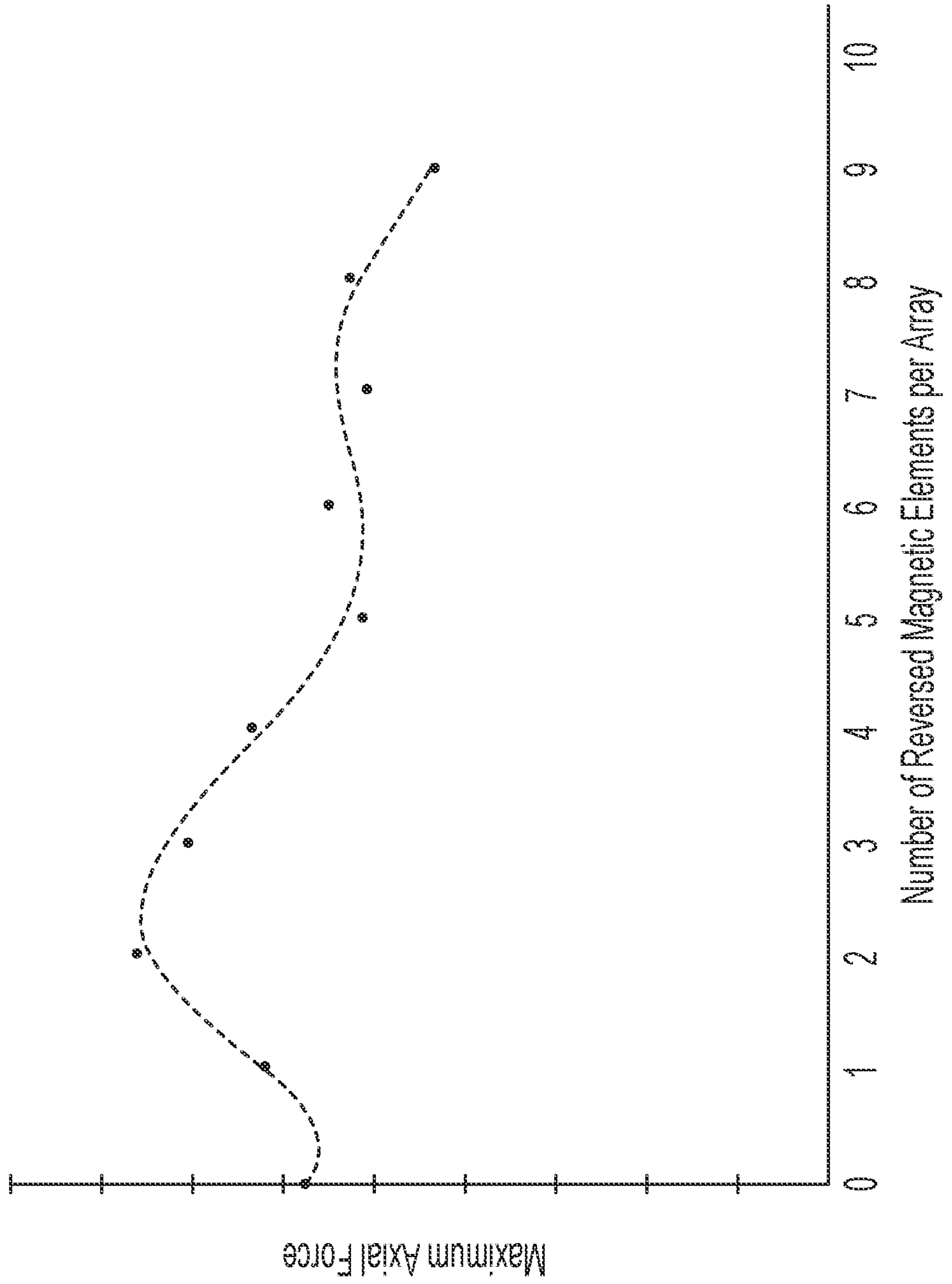
FIG. 2 generally depicts a graph depicting attractive force between the catheters of the system based on the number of opposite poled magnetic elements within an array of magnetic elements, according to one or more embodiments shown and described herein.

The relative sizes of the first magnetic segments 122, 142, 222, 242 and the second magnetic segments 124, 144, 224, 244 may causes changes to the amount of attractive force between the first catheter 100 and the second catheter 200. For example, wherein the proximal and distal magnetic arrays 120, 140, 220, and 240 have 30 magnetic elements each all having the same size, magnetic strength, and shape, the number of magnetic elements in the second magnetic segments 124, 144, 224, 244 may affect the force of attraction between the first catheter 100 and the second catheter 200 and therefore the amplitude of the resultant tactile feedback felt as a result of aligning the first catheter 100 and the second catheter 200. For example, FIG. 2 depicts a graph illustrating the relationship between the axial attractive force (y-axis) between the first catheter 100 and the second catheter 200 against the number of magnetic elements (x-axis) within the second magnetic segments 124, 144, 224, 244. As depicted a maximum attractive force between the first catheter 100 and the second catheter 200 may be achieved when second magnetic segments 124, 144, 224, 244 contain two magnetic elements. Accordingly, in such embodiment, in each array of 30 magnetic elements, two of the magnetic elements (making up the second magnetic segment) are positioned in opposite polarity to the remaining 28 magnetic elements (making up the first magnetic segment). It is noted that the number of magnetic elements may vary depending on the overall length of the particular arrays.

It is noted that the catheters 100, 200 and the accompanying magnetic elements may be sized and/or shaped to be advanced through any target blood vessel. For example, blood vessels having an internal diameter of about 3 mm, it may be desirable to configure any the magnetic elements to be less than about 3 mm in diameter/width. In some embodiments, the catheters 100, 200 may have any suitable diameter for intravascular use, such as, for example, about 4 French (1.33 mm), about 5.7 French (1.9 mm), about 6.1 French (6.03 mm), about 7 French (2.33 mm), about 8.3 French (2.77 mm), or a value between about 4 French (1.33 mm) and about 9 French (3.0 mm), between about 4 French (1.33 mm) and about 7 French (2.33 mm), between about 4 French (1.33 mm) and about 6 French (2.0 mm), or the like. In embodiments, each magnetic elements may have any suitable length in an axial direction of a catheter (e.g., about 5 mm, about 10 mm, about 15 mm, about 20 mm, or the like).

The individual magnetic elements described herein may be permanent magnets comprising one or more hard magnetic materials, such as but not limited to alloys of rare earth elements (e.g., samarium-cobalt magnets or neodymium magnets, such as N52 magnets) or alnico. In some variations, the magnets may comprise anisotropic magnets; in other variations, the magnets may comprise isotropic magnetics. In some variations, the magnets may be formed from compressed powder. In some variations, a portion of magnetic elements may comprise one or more soft magnetic materials, such as but not limited to iron, cobalt, nickel, or ferrite. It should be appreciated that in systems comprising two catheters, either the first catheter 100 or the second catheter 200 may comprise ferromagnetic elements (i.e., elements attracted to but not generating a permanent magnetic field). For example, in some variations, the first catheter 100 may include one or more ferromagnetic elements while the second catheter 200 may comprise one or more permanent magnets. In other variations, the second catheter 200 may include one or more ferromagnetic elements while the first catheter 100 may comprise one or more permanent magnets. However, in other variations, one or both of the first catheter 100 and the second catheter 200 may include any suitable combination of ferromagnetic, permanent, and/or other suitable kinds of magnets. It is noted that the proximal and distal magnetic arrays 120, 140, 220, 240 on either side of the treatment portions 130, 230 may aid in providing improved and even coaptation between the treatment portions 130, 230 during treatment.

Figure 3:
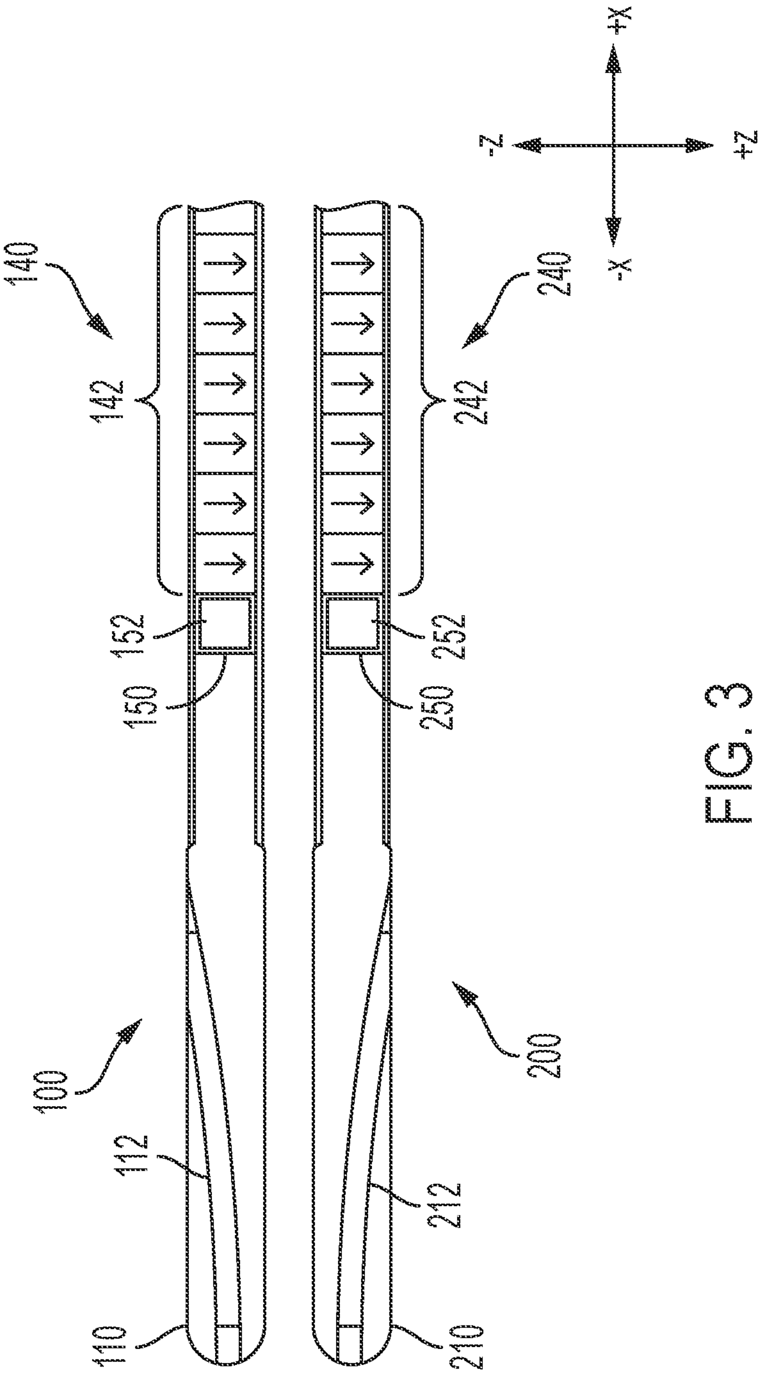
FIG. 3 schematically depicts a cross sectional view of a distal tip of a first catheter and a second catheter of the system of FIG. 1, according to one or more embodiments shown and described herein.

Referring to FIG. 3, the distal tip 110, 210 of the catheters 100, 200 are generally depicted. As depicted, the catheters 100, 200 may have a lumen 112, 212 or a through hole extending through the distal tip 110 to provide a rapid exchange tip. For example, the lumen 112, 212 may be configured to pass a guidewire and allow tracking of the catheter over the guidewire.

Still referring to FIG. 3, the catheters 100, 200 described herein may comprise one or more visual alignment aids for directly or indirectly visualizing alignment of catheters with respect to each other. Rotational alignment of the catheters 100, 200 may be difficult to discern. Fluoroscopically visualized rotational indicators, may enable better rotational alignment of catheters 100, 200 relative to each other, and may also help with axial alignment. One variation of a rotational indicator 150, 250 may have a cube shape (though other shapes are contemplated and possible) with a corresponding cube-shaped cut-out 152, 252. A thickness of the cube may vary for differing indicator thicknesses. Rotational indicators of various configurations may allow a user to visually match an orientation of a rotational indicator in a first catheter 100 to an orientation of a rotational indicator in a second catheter 200. For example, rotational indicators may include any shape cut out (e.g., circular, arrow-shaped, rectangular, letter shaped, star-shaped, etc.) to allow a user to visualize when proper rotational and/or axial alignment is achieved.

As depicted in FIG. 3, the rotational indicator 150, 250 of the catheters 100, 200 may be disposed between the distal tip 110, 210 and a distal magnetic array 140, 240. The catheters 100 and 200 may be determined to be rotationally aligned with respect to each other and in position for fistula formation when the rotational indicators 150, 250 appear to face the same direction via fluoroscopic visualization. When the catheters 100 and 200 are rotationally aligned, the treatment portion 130 of the first catheter 100 may be arranged to face the treatment portion 230 of the second catheter 200 such that a fistula may be formed with and between the treatment portions 130, 230. It is noted that the rotational indicators 150, 250 are not limited to a location near the distal ends of the catheters 100 and 200 and may be provided anywhere along the catheters 100 and 200.

Figure 4:
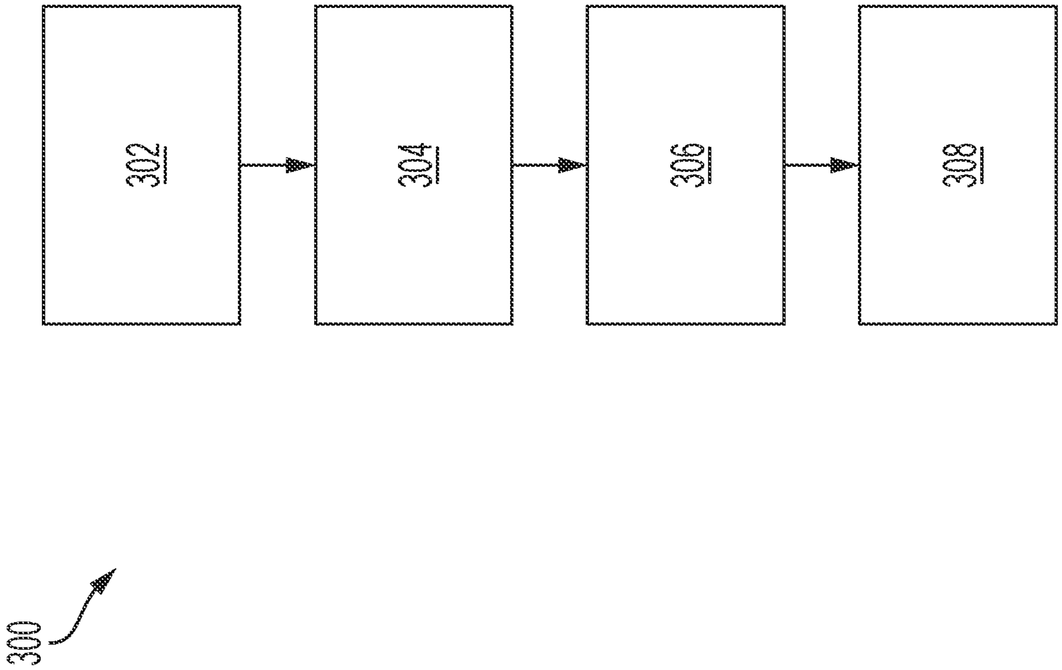
FIG. 4 depicts a flow chart illustrating a method for treating a blood vessel, according to one or more embodiments shown and described herein.

Referring now to FIG. 4, a flow chart illustrating a method 300 of forming a fistula is generally depicted. It is noted that the method 300 may include a greater or fewer number of steps, taken in any order, without departing from the scope of the present disclosure. It is noted that the method 300 illustrated in FIG. 4 may be best understood when reviewed in conjunction with FIGS. 5A-5D which generally illustrate alignment and treatment of a blood vessel using the first and second catheters 100, 200 as described herein.

Figure 5A:
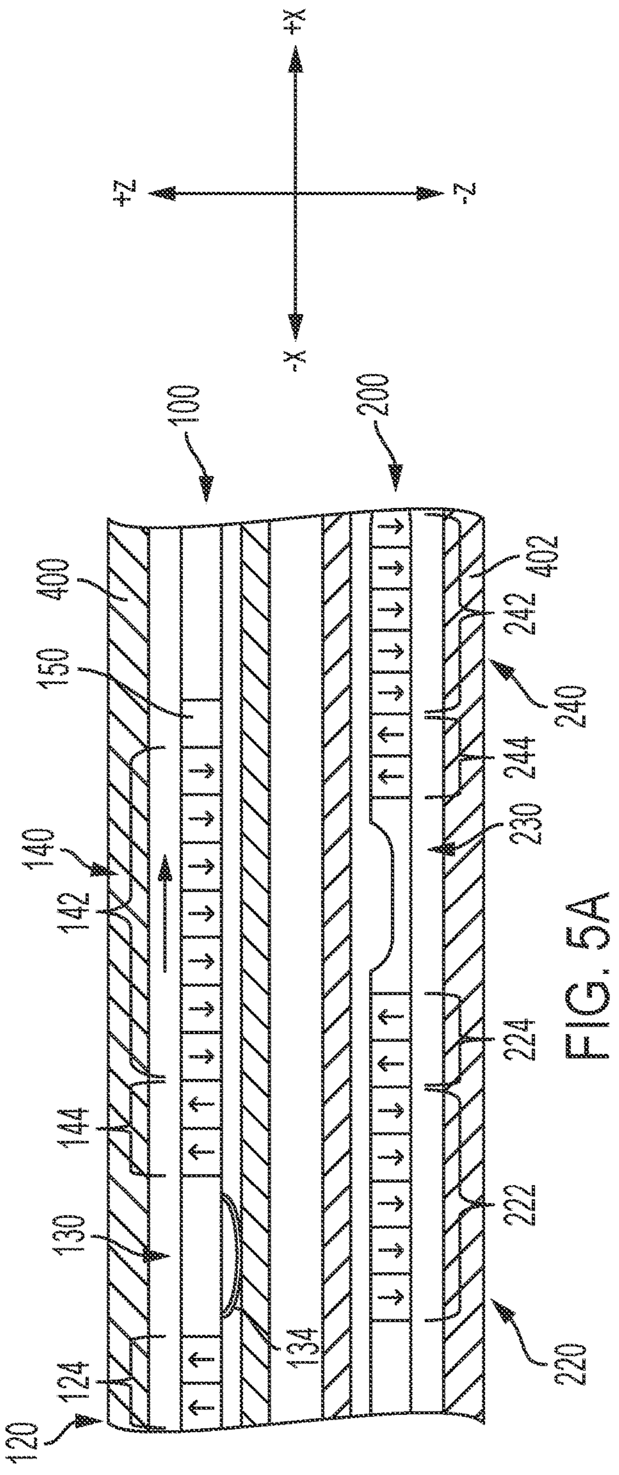
FIG. 5A schematically depicts a first catheter of the system of FIG. 1 being advanced through a first blood vessel and a second catheter of the system of FIG. 1 being advanced through a second vessel, according to one or more embodiments shown and described herein.

Still referring to FIG. 4, at block 302 the method 300 includes advancing the first catheter 100 through a first blood vessel 400 as depicted in FIG. 5A. For example, a user may advance the first catheter 100 through the first blood vessel 400 to a first treatment location so that the treatment portion 130 is advanced to the first treatment location.

Referring again to FIG. 4, at block 304 the method 300 further includes advancing the second catheter 200 through a second blood vessel 402. For example, and as depicted in FIG. 5A, the user may advance the second catheter 200 through the second blood vessel 402 to a second treatment location in the second vessel. It is noted that the first blood vessel 400 and the second blood vessel 402 may be adjacent vessels such as a vein and an artery, though vein to vein and artery to artery treatments are contemplated and possible.

Figure 5B:
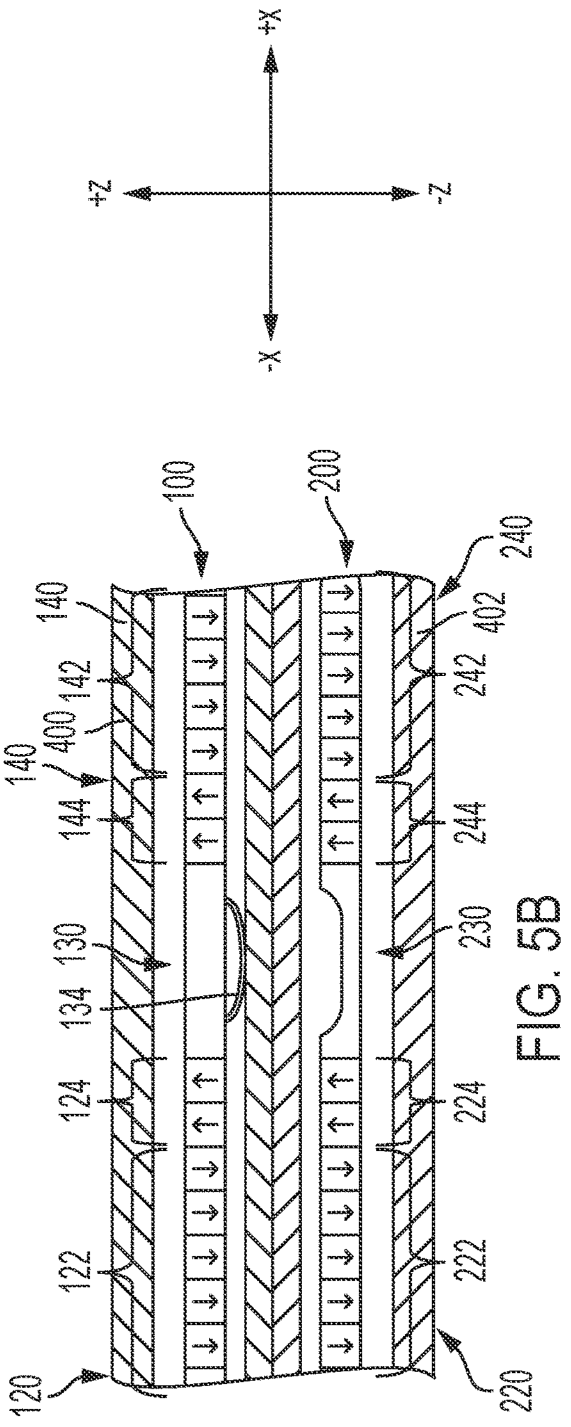
FIG. 5B schematically depicts alignment of the first catheter and the second catheter of FIG. 5A, according to one or more embodiments shown and described herein.

The second location may be substantially aligned with the first location, as depicted in FIG. 5B. During advancement of the first catheter 100 and/or the second catheter 200 a mismatch in polarity between the first magnetic segments 122, 142 of the first catheter 100 with the second magnetic segments 224, 244 of the second catheter 200 (and a mismatch in polarity between the second magnetic segments 124, 144 of the first catheter 100 with the first magnetic segments 222, 242 causes the first catheter 100 to be at least partially repelled from the second catheter 200 while the treatment portions 130, 230 of the first and second catheters 100, 200 are out of alignment. in the +/−X direction of the depicted coordinate axes.

Figure 5C:
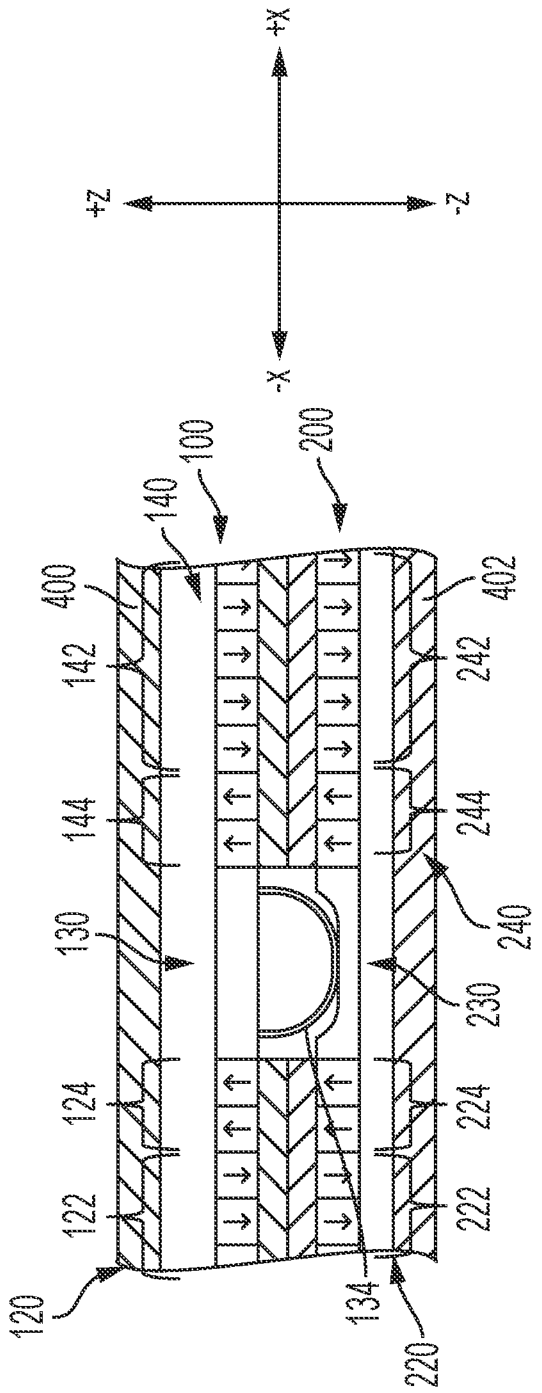
FIG. 5C Schematically depicts treatment of the first blood vessel and the second blood vessel with the first catheter and the second catheter of FIG. 5B, according to one or more embodiments shown and described herein.

Referring again to FIG. 4, at block 306 the method 300 includes aligning the treatment portion 130 may the first catheter 100 with the treatment portion 230 of the second catheter 200. For example, as depicted in FIGS. 5B and 5C, once the treatment portions 130, 230 of the first catheter 100 and the second catheter 200 are aligned (e.g., both longitudinally and rotationally) the first and second catheters 100 may become attracted to one another via attraction between the first magnetic segments 122, 142 of the first catheter 100 and the first magnetic segments 222, 242 of the second catheter 200 and attraction between the second magnetic segments 124, 144 of the first catheter 100 and the second magnetic segments 224, 244 of the second catheter 200. The sudden change in attraction between the first and second catheters 100, 200 may cause the first catheter 100 and the second catheter 200 to snap together, thereby pulling the first blood vessel 400 and the second blood vessel 402 into contact with one another, as illustrated in FIG. 5C. Accordingly, once aligned, the first catheter 100 and the second catheter 200 may coapt together and sandwich tissue for the first vessel and the second vessel therebetween. The snapping effect caused by the magnetic attraction between the first catheter 100 and the second catheter 200 may cause tactile feedback which may be felt by a user and provide an indication of proper longitudinal alignment between the first catheter 100 and the second catheter 200. In some embodiments, the method 300 may further include confirming alignment of the first catheter 100 and the second catheter 200 via fluoroscopy or other imaging techniques.

Figure 5D:
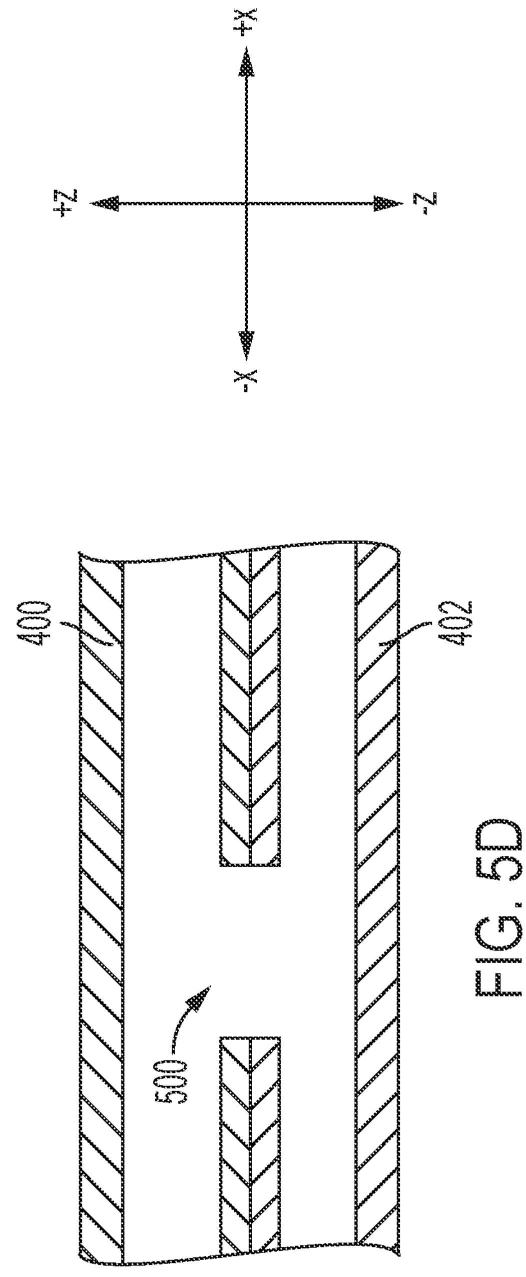
FIG. 5D schematically depicts a fistula formed between the first blood vessel and the second blood vessel, according to one or more embodiments shown and described herein.

Referring again to FIG. 4, at block 308 the method 300 may further include, after alignment between the treatment portions 130, 230 of the first catheter 100 and the second catheter 200, performing a vascular treatment procedure to modify the first blood vessel 400 and/or the second blood vessel 402 at the first treatment location and/or the second treatment location. For example, the fistula-forming element 134 of the treatment portion 130 may be activated to ablate tissue of the first blood vessel 400 and the second blood to form a fistula 500 between the first blood vessel 400 and the second blood vessel 402, as generally depicted in FIG. 5D. Upon formation of the fistula 500 the first catheter 100 and the second catheter 200 may be withdrawn from the respective first blood vessel 400 and the second blood vessel 402.

Embodiments can be described with reference to the following numerical clause:

1. A catheter for endovascular treatment of a blood vessel, the catheter comprising: a treatment portion, a proximal magnetic array positioned proximal to the treatment portion, and a distal magnetic array positioned distal to the treatment portion, wherein each of the proximal magnetic array and the distal magnetic array comprise: a first magnetic segment having a first polarity; and a second magnetic segment having a second polarity opposite to the first polarity, wherein the second magnetic segment is disposed adjacent to the treatment portion.

2. The catheter for endovascular treatment of a blood vessel of any preceding clause, wherein a length of the first magnetic segment is different from a length of the second magnetic segment.

3. The catheter for endovascular treatment of a blood vessel of any preceding clause, wherein the first magnetic segment comprises a length that is longer than a length of the second magnetic segment.

4. The catheter for endovascular treatment of a blood vessel of any preceding clause, wherein the second magnetic segment comprises at least two magnetic elements.

5. The catheter for endovascular treatment of a blood vessel of any preceding clause, wherein magnetic elements of the first and the second magnetic segments have substantially a same shape.

6. The catheter for endovascular treatment of a blood vessel of any preceding clause, wherein magnetic elements of the first and the second magnetic segments have equal magnetic strengths.

7. The catheter for endovascular treatment of a blood vessel of any preceding clause, wherein the second magnetic segment is disposed directly adjacent to the treatment portion so as to be positioned between the first magnetic segment and the treatment portion.

8. The catheter for endovascular treatment of a blood vessel of any preceding clause, wherein the treatment portion comprises an electrode.

9. The catheter for endovascular treatment of a blood vessel of any preceding clause, further comprising a housing in which the electrode is disposed.

10. The catheter for endovascular treatment of a blood vessel of any preceding clause, further comprising a rotational indicator configured to indicate a rotational alignment of the catheter.

11. The catheter for endovascular treatment of a blood vessel of any preceding clause, wherein the second magnetic segment of the proximal magnetic array has a same polarity as the second magnetic segment of the distal magnetic array.

12. A system for endovascular treatment of a blood vessel, the system comprising: a first catheter and a second catheter, each of the first catheter and the second catheter comprising a treatment portion, a proximal magnetic array positioned proximal to the treatment portion, and a distal magnetic array positioned distal to the treatment portion, wherein each proximal magnetic array and each distal magnetic array comprises: a first magnetic segment having a first polarity; and a second magnetic segment having a second polarity opposite to the first polarity of the first magnetic segment, the second magnetic segment is disposed adjacent to the treatment portion, wherein the second polarity of second magnetic segment of the first catheter has a same polarity orientation as the second magnetic segment of the second catheter when the first catheter and the second catheter are aligned for endovascular treatment.

13. The system for endovascular treatment of a blood vessel of any preceding clause, wherein each of the second magnetic segments of the first catheter and the second catheter has substantially a same length.

14. The system for endovascular treatment of a blood vessel of any preceding clause, wherein each of the second magnetic segments of the first catheter and the second catheter has substantially a same magnetic strength.

15. The system for endovascular treatment of a blood vessel of any preceding clause, wherein the second magnetic segments of the first catheter attract the second magnetic segments of the second catheter when the second magnetic segments of the first catheter are aligned with the second magnetic segments of the second catheter.

16. The system for endovascular treatment of a blood vessel of any preceding clause, wherein alignment of the treatment portions of the first and second catheters generates tactile feedback to a user.

17. A method for endovascular treatment of a blood vessel comprising: advancing a first catheter within a first blood vessel to a treatment location; aligning a treatment portion of the first catheter with the treatment location, wherein the first catheter comprises: a proximal magnetic array positioned proximal to the treatment portion, and a distal magnetic array positioned distal to the treatment portion, wherein each of the proximal magnetic array and the distal magnetic array comprises: a first magnetic segment having a first polarity; and a second magnetic segment having a second polarity opposite to the first polarity, the second magnetic segment being disposed adjacent to the treatment portion; and modifying the first blood vessel at the treatment location with the treatment portion.

18. The method of any preceding clause, further comprising: advancing a second catheter within a second blood vessel to the treatment location; and aligning a treatment portion of the second catheter with the treatment portion of the first catheter, wherein the second catheter comprises: a proximal magnetic array positioned proximal to the treatment portion, and a distal magnetic array positioned distal to the treatment portion, wherein each of the proximal magnetic array and the distal magnetic array comprise: a first magnetic segment comprising the second polarity; and a second magnetic segment comprising the first polarity, the second magnetic segment being disposed adjacent to the treatment portion.

19. The method of any preceding clause, wherein modifying the first blood vessel at the treatment location comprises forming a fistula between the first blood vessel and the second blood vessel with the treatment portions of the first and second catheters.

20. The method of any proceeding clause, wherein alignment of the treatment portion of the first catheter and the second catheter generates tactile feedback.

It should now be understood that embodiments of the present disclosure are directed to devices, systems, and methods for forming a fistula between two blood vessels. In some embodiments, the devices and methods may be used to form a fistula between two blood vessels. More particularly, a catheter may be placed in each of two adjacent blood vessels to form a fistula therebetween with the catheters. For example, in some embodiments, a catheter for endovascular treatment of a blood vessel includes a treatment portion, a proximal magnetic array positioned proximal to the treatment portion, and a distal magnetic array positioned distal to the treatment portion. Each of the proximal magnetic array and the distal magnetic array includes a first magnetic segment having a first polarity and a second magnetic segment having a second polarity opposite to the first polarity, the second magnetic segment is disposed adjacent to the treatment portion. The opposite poled magnetic segments may provide improved coaptation with a second catheter, as will be described in greater detail herein, and tactile feedback (e.g., vibration, snapping into place feeling, or the like) to ensure proper alignment and/or coaptation. These and additional features and benefits will be described in greater detail herein.

It is noted that the terms “substantially” and “about” may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A catheter for endovascular treatment of a blood vessel, the catheter comprising:

a treatment portion, a proximal magnetic array positioned proximal to the treatment portion, and a distal magnetic array positioned distal to the treatment portion, wherein each of the proximal magnetic array and the distal magnetic array comprise:

a first magnetic segment comprising a first contiguous block of like-polarity magnets, said first magnetic segment having a first polarity; and a second magnetic segment comprising a second contiguous block of like-polarity magnets, said second magnetic segment having a second polarity opposite to the first polarity, wherein the second magnetic segment is disposed adjacent to the treatment portion.

2. The catheter for endovascular treatment of a blood vessel of claim 1, wherein a length of the first magnetic segment is different from a length of the second magnetic segment.

3. The catheter for endovascular treatment of a blood vessel of claim 1, wherein the first magnetic segment comprises a length that is longer than a length of the second magnetic segment.

4. The catheter for endovascular treatment of a blood vessel of claim 1, wherein the second magnetic segment comprises at least two magnetic elements.

5. The catheter for endovascular treatment of a blood vessel of claim 1, wherein magnetic elements of the first and the second magnetic segments have substantially a same shape.

6. The catheter for endovascular treatment of a blood vessel of claim 1, wherein magnetic elements of the first and the second magnetic segments have equal magnetic strengths.

7. The catheter for endovascular treatment of a blood vessel of claim 1, wherein the second magnetic segment is disposed directly adjacent to the treatment portion so as to be positioned between the first magnetic segment and the treatment portion.

8. The catheter for endovascular treatment of a blood vessel of claim 1, wherein the treatment portion comprises an electrode.

9. The catheter for endovascular treatment of a blood vessel of claim 8, further comprising a housing in which the electrode is disposed.

10. The catheter for endovascular treatment of a blood vessel of claim 1, further comprising a rotational indicator configured to indicate a rotational alignment of the catheter.

11. The catheter for endovascular treatment of a blood vessel of claim 1, wherein the second magnetic segment of the proximal magnetic array has a same polarity as the second magnetic segment of the distal magnetic array.

12. The catheter for endovascular treatment of a blood vessel of claim 1, wherein the first contiguous block of like-polarity magnets and the second contiguous block of like-polarity magnets are not interrupted by intervening magnetic elements.

13. A system for endovascular treatment of a blood vessel, the system comprising:

a first catheter and a second catheter, each of the first catheter and the second catheter comprising a treatment portion, a proximal magnetic array positioned proximal to the treatment portion, and a distal magnetic array positioned distal to the treatment portion, wherein each proximal magnetic array and each distal magnetic array comprises:

a first magnetic segment comprising a first contiguous block of like-polarity magnets, said first magnetic segment having a first polarity; and a second magnetic segment comprising a second contiguous block of like-polarity magnets, said second magnetic segment having a second polarity opposite to the first polarity of the first magnetic segment, the second magnetic segment is disposed adjacent to the treatment portion, wherein the second polarity of second magnetic segment of the first catheter has a same polarity orientation as the second magnetic segment of the second catheter when the first catheter and the second catheter are aligned for endovascular treatment.

14. The system for endovascular treatment of a blood vessel of claim 13, wherein each of the second magnetic segments of the first catheter and the second catheter has substantially a same length.

15. The system for endovascular treatment of a blood vessel of claim 13, wherein each of the second magnetic segments of the first catheter and the second catheter has substantially a same magnetic strength.

16. The system for endovascular treatment of a blood vessel of claim 13, wherein the second magnetic segments of the first catheter attract the second magnetic segments of the second catheter when the second magnetic segments of the first catheter are aligned with the second magnetic segments of the second catheter.

17. The system for endovascular treatment of a blood vessel of claim 16, wherein alignment of the treatment portions of the first and second catheters generates tactile feedback to a user.

18. A method for endovascular treatment of a blood vessel comprising:

advancing a first catheter within a first blood vessel to a treatment location;

aligning a treatment portion of the first catheter with the treatment location, wherein the first catheter comprises:

a proximal magnetic array positioned proximal to the treatment portion, and a distal magnetic array positioned distal to the treatment portion, wherein each of the proximal magnetic array and the distal magnetic array comprises:

a first magnetic segment comprising a first contiguous block of like-polarity magnets, said first magnetic segment having a first polarity; and a second magnetic segment comprising a second contiguous block of like-polarity magnets, said second magnetic segment having a second polarity opposite to the first polarity, the second magnetic segment being disposed adjacent to the treatment portion; and modifying the first blood vessel at the treatment location with the treatment portion.

19. The method of claim 18, further comprising:

advancing a second catheter within a second blood vessel to the treatment location; and aligning a treatment portion of the second catheter with the treatment portion of the first catheter, wherein the second catheter comprises:

a proximal magnetic array positioned proximal to the treatment portion, and a distal magnetic array positioned distal to the treatment portion, wherein each of the proximal magnetic array and the distal magnetic array comprise:

a first magnetic segment comprising the second polarity; and a second magnetic segment comprising the first polarity, the second magnetic segment being disposed adjacent to the treatment portion.

20. The method of claim 19, wherein modifying the first blood vessel at the treatment location comprises forming a fistula between the first blood vessel and the second blood vessel with the treatment portions of the first and second catheters.

21. The method of claim 19, wherein alignment of the treatment portion of the first catheter and the second catheter generates tactile feedback.

* * * * *